(12) United States Patent
Andersen et al.

(10) Patent No.: US 7,599,591 B2
(45) Date of Patent: Oct. 6, 2009

(54) OPTICAL DELIVERY SYSTEMS AND METHODS OF PROVIDING ADJUSTABLE BEAM DIAMETER, SPOT SIZE AND/OR SPOT SHAPE

(75) Inventors: Dan E. Andersen, Menlo Park, CA (US); David G. Angeley, Charlottesville, VA (US); Philip Gooding, Mountain View, CA (US); Michael W. Wiltberger, Santa Clara, CA (US); David H. Mordaunt, Los Gatos, CA (US)

(73) Assignee: Optimedica Corporation, Santa Clara, CA (US)

( * ) Notice: Subject to any disclaimer, the term of this patent is extended or adjusted under 35 U.S.C. 154(b) by 440 days.

(21) Appl. No.: 11/653,663

(22) Filed: Jan. 12, 2007

(65) Prior Publication Data
US 2007/0189664 A1 Aug. 16, 2007

Related U.S. Application Data

(60) Provisional application No. 60/758,802, filed on Jan. 12, 2006.

(51) Int. Cl.
*G02B 6/06* (2006.01)
(52) U.S. Cl. ........................ 385/115; 385/116; 385/117; 385/118; 606/182
(58) Field of Classification Search ................... 385/25, 385/31–37, 115–119; 600/182, 342, 478; 606/13, 16
See application file for complete search history.

(56) References Cited

U.S. PATENT DOCUMENTS

| 3,703,176 | A | 11/1972 | Vassiliadis et al. |
|---|---|---|---|
| 4,576,160 | A | 3/1986 | Tanaka |
| 4,628,416 | A | 12/1986 | Dewey |
| 4,917,486 | A | 4/1990 | Raven et al. |
| 5,391,165 | A | 2/1995 | Fountain et al. |
| 5,688,264 | A | 11/1997 | Ren et al. |
| 6,014,204 | A * | 1/2000 | Prahl et al. .................... 356/73 |
| 6,099,522 | A | 8/2000 | Knopp et al. |
| 6,717,745 | B2 | 4/2004 | Nemes |
| 7,146,983 | B1 | 12/2006 | Hohla et al. |
| 2004/0073120 | A1 | 4/2004 | Motz et al. |
| 2006/0100677 | A1 | 5/2006 | Blumenkranz et al. |
| 2007/0147730 | A1 | 6/2007 | Wiltberger et al. |
| 2007/0269173 | A1* | 11/2007 | Lu .............................. 385/117 |
| 2009/0003764 | A1* | 1/2009 | Ridder et al. ................. 385/14 |

(Continued)

OTHER PUBLICATIONS

Helmchen, F. "Dynamic Confocal Imaging Of Living Brain Miniaturization Of Fluorescence Microscopes Using Fibre Optics", Presented at a workshop held at the University of Bristol supported by The Physiological Society, [online] Jun. 30, 2001, retrieved from the Internet: http://www.blackwell-synergy.com/doi/pdf/10.1113/eph8702478.

* cited by examiner

*Primary Examiner*—Hemang Sanghavi
(74) *Attorney, Agent, or Firm*—DLA Piper LLP (US)

(57) ABSTRACT

An optical device and method for varying an optical characteristic of an optical beam can include a plurality of optical fibers each having an input end, an output end, and a core, wherein each of the optical fibers has an effective area and a numerical aperture, and a beam-deviating component for moving at least one of the optical fiber input ends and the optical beam relative to each other such that the optical beam selectively enters the input ends one at a time and is transmitted out the output ends one at a time, wherein at least one of the effective areas and the numerical apertures varies among the plurality of optical fibers such that the optical beam transmitted out of the output ends has a varying optical characteristic.

37 Claims, 10 Drawing Sheets

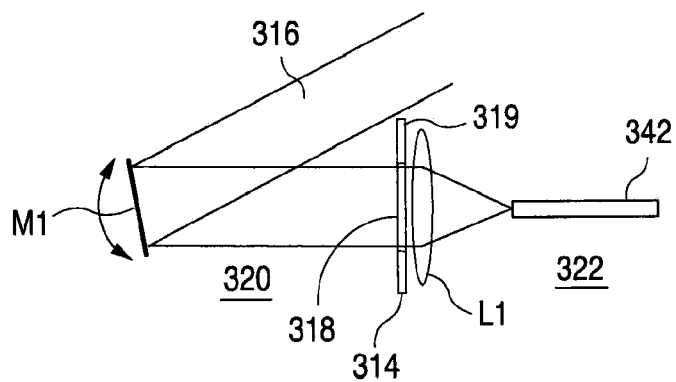
FIG. 9A
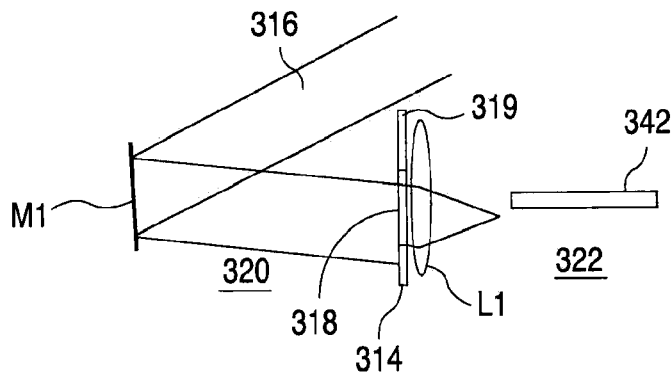
FIG. 9B
FIG. 10A
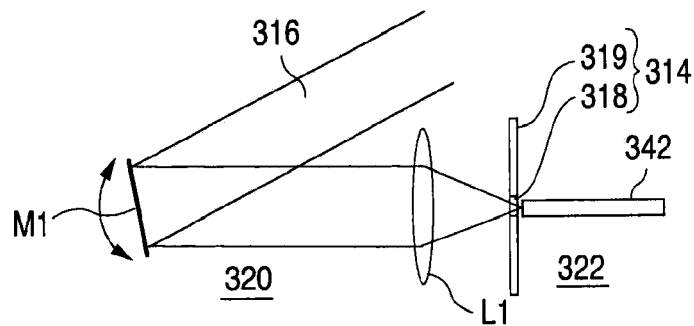
FIG. 10B
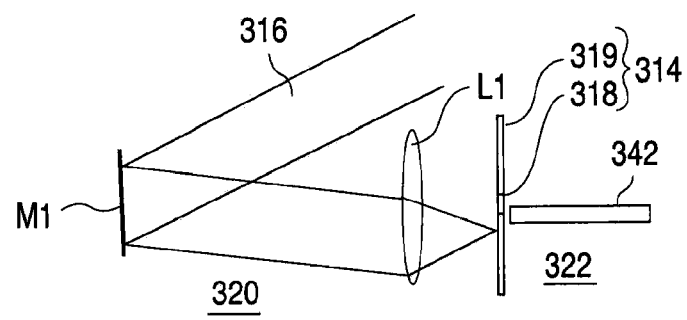

OPTICAL DELIVERY SYSTEMS AND METHODS OF PROVIDING ADJUSTABLE BEAM DIAMETER, SPOT SIZE AND/OR SPOT SHAPE

CROSS REFERENCE TO RELATED APPLICATIONS

This application claims the benefit of priority U.S. Provisional Application No. 60/758,802 filed on Jan. 12, 2006, the entire content of which is incorporated herein by reference.

BACKGROUND OF THE INVENTION

1. Field of the Invention

The present invention pertains to systems and methods for producing adjustable beams, spot sizes and spot shapes on a target.

2. Background Information

Today, many ophthalmic treatments involve using an optical beam to treat a target (e.g., a patient's eye). For example, diabetic retinopathy and age-related macular degeneration are subject to photocoagulative treatment with visible laser light. In performing these treatments, it is sometimes advantageous to be able to use beams of different sizes depending on the particular type of treatment and the condition of the patient. Traditionally, adjustable optical beam diameters have been produced by using a fixed light source with either a zoom lens or a turret assembly to vary the magnification level. Alternatively, the optical beam has been defocused by changing the distance between the target and the last lens in the chain of optical elements to vary the beam spot size. While these methods vary the beam spot size satisfactorily, these methods involve moving elements with large moments of inertia. Having to move elements makes the system expensive to build and operate and, more importantly, limits the speed at which the beam spots can be adjusted.

A system using a zoom lens has additional problems stemming from the second law of thermodynamics which, in the context of optics, makes the source the brightest part of the system. A system's optical invariant is represented by the following equation:

$$\text{Invariant}(I) = y_p n u - y n u_p$$

where $y_p$ and $u_p$ are the height and slope angle of the principle ray and y and u are the height and slope angle of the marginal ray and n is the index of refraction At the object and conjugate image planes, the Invariant reduces to:

Object plane: $I = h_o n_o u_o$  Image Plane: $I = h_i n_i u_i$ where h is the height of the object/image and the subscripts $_o$ and $_i$ denote the object and image locations.

In the context of this application, the paraxial approximation dominates and the product nu can be replaced with NA, numerical aperture. Therefore, the optical invariant can be written:

$$I = h_o(NA)_o = h_i(NA)_i$$

Magnification of the optical system is:

$$M = h_i/h_o = (NA)_o/(NA)_i$$

wherein M=magnification level,
$(NA)_O$=numerical aperture on the object side, and
$(NA)_i$=numerical aperture on the image side of the system.

If a single object is used, the image side numerical aperture will therefore decrease with increasing image spot size. Because the use of larger spot sizes requires proportionally higher power to cause the desired effect on the target (e.g., drilling a hole or heating tissues), this inverse relationship between large spot size and small numerical aperture poses a problem when there is an intermediate structure between the source and target. For example, these intermediate structures can often absorb enough of the delivered light to cause damage to itself and the system. This may occur, for example, in the case of transpupilary retinal photocoagulation.

There is a need for systems to have the ability to vary spot size at the treatment plane. The spot size variation allows for flexible adaptation of treatment fluences and geometries. Furthermore it is also practical to have the ability to easily switch the treatment beam on and off without disrupting the stability of the light source for instance. It is further advantageous to have the ability to scan a pattern of treatment light on the targeted structure. This scanning ability overcomes the tedium and duration of treatment when single spots are laid down one at a time. The present invention meets the needs of; varying spot size; switching the treatment light off/on; and scanning and does so in an efficient manner using a well balanced distribution of the attending functions in an economical and compact package.

In the described embodiments, the switching mechanism is achieved via a galvanometric (galvo) moving mirror technique at the input to the fiber. The galvo mirror technique is economical while achieving appropriate on/off switching times, however other means of optically deviating the beam are also considered.

Scanning in the treatment area is also achieved using galvanometric moving mirrors using a separate set of mirrors on the output side of the fiber. Once again, the choice of a galvo technique is economical and compact while achieving adequate scan range, resolution, and speed.

Adjustment of the spot size at the treatment plane has been achieved traditionally in several different ways. One simple technique is to defocus the beam at the treatment plane. The defocus technique has the disadvantage of deviating from the image plane and therefore an uncertain change in irradiance distribution. There is also the loss of the sharp edge definition of the spot and the safety issue of the positioning a small beam at some location other than the treatment plane. Another method to vary spot size is to employ a variable magnification optical system. This can be done by inserting and replacing sections of the optical systems as in a turret design. A zoom lens configuration whereby axial distances between lenses are adjusted can also be used. Both the turret and zoom lens configurations involve movement of powered optics and therefore the associate disadvantages in reliability and alignment. Also the lens systems are complex and the optical performance is a weighted compromise over all possible configurations. This is particularly true for a zoom lens design.

Moreover, traditional approaches relate only to limited aspects of the overall etendue transfer characteristics of interest, such as magnification or aperture size change in one optical element as described immediately above. Consideration of the overall etendue, or changes in etendue as a function of one or both of fiber-related parameters or variations resulting from optical elements that modify an effective etendue of a beam, is based on the relationship set forth by the basic expression of this invariant (luminosity, throughput, or etendue), or "G," represented by the following equation:

$$G = n^2 A \Omega$$

wherein A is the area of the entrance pupil of the optical element,

Ω is the solid angle subtended at this pupil by the ray, and n is the refractive index of the media between the two.

The optical invariant, I, is the reduction of the etendue to its linear or one dimensional form and may be more commonly known.

This relationship should also be considered in connection with those pertaining to magnification and numerical aperture, as set forth above. Therefore, drawbacks exist for system that are unable to change beam diameter, spot size and spot shape via changes to one or more of fiber diameter (core size), effective fiber diameter (and/or effective numerical aperture), aperture size, and entendue-modifying aspects such as aperture placement, among others that may be varied vis-á-vis application of the above-stated relationships to elements or articles of optical systems.

Accordingly, apparatus and methods for providing adjustable beams, spot sizes, and spot shapes without the above-described limitations and disadvantages are desired.

SUMMARY

The innovations herein solve the aforementioned problems by modifying optical characteristics of beams, by varying objects such as fibers or other optical elements, adjusting one or more etendue-modifying aspects, etc., to achieve a final beam diameter of desired size and shape.

An optical device consistent with aspects of the innovations herein can include a device for generating an optical beam, a plurality of optical fibers each having an input end, an output end, and a core, wherein each of the optical fibers has an effective area and a numerical aperture, and a device for moving at least one of the optical fiber input ends and the optical beam relative to each other such that the optical beam selectively enters the input ends one at a time and is transmitted out the output ends one at a time, wherein at least one of the effective areas and the numerical apertures varies among the plurality of optical fibers such that the optical beam transmitted out of the output ends has a varying optical characteristic.

An array of fibers consistent with aspects of the innovations herein, and used to adjust a treatment beam in a photomedical device, can include a plurality of optical fibers each having an input end, an output end, and a core, wherein each of the optical fibers has an effective area and a numerical aperture, and an optical component configured for association with a beam-deviating element so as to enable selective injection or ejection of an optical beam into the input end or out of the output end, wherein at least one of the effective areas and the numerical apertures varies among the plurality of optical fibers such that a transmitted optical beam has a varying optical characteristic.

A method of varying an optical characteristic of an optical beam consistent with aspects of the innovations here can include generating an optical beam suitable for transmission by at least one of a plurality of optical fibers that each have an input end, an output end, and a core, wherein each of the optical fibers has an effective area and a numerical aperture, and directing the optical beam via a deviation with regard to the optical fiber input ends or the optical beam relative to each other such that the optical beam selectively enters the input ends one at a time and is transmitted out the output ends one at a time, wherein at least one of the effective areas and the numerical apertures varies among the plurality of optical fibers such that the optical beam transmitted out of the output ends has a varying optical characteristic.

Other aspects and features of the present invention will become apparent by a review of the specification, claims and appended figures.

BRIEF DESCRIPTION OF THE DRAWINGS

FIGS. 9A, 9B, 10A, 10B, 11A and 11B are diagrams illustrating injection of light into fibers, each with differing placement of moving elements associated with exemplary switches consistent with one or more aspects of the present invention.

DETAILED DESCRIPTION

Figure 1:
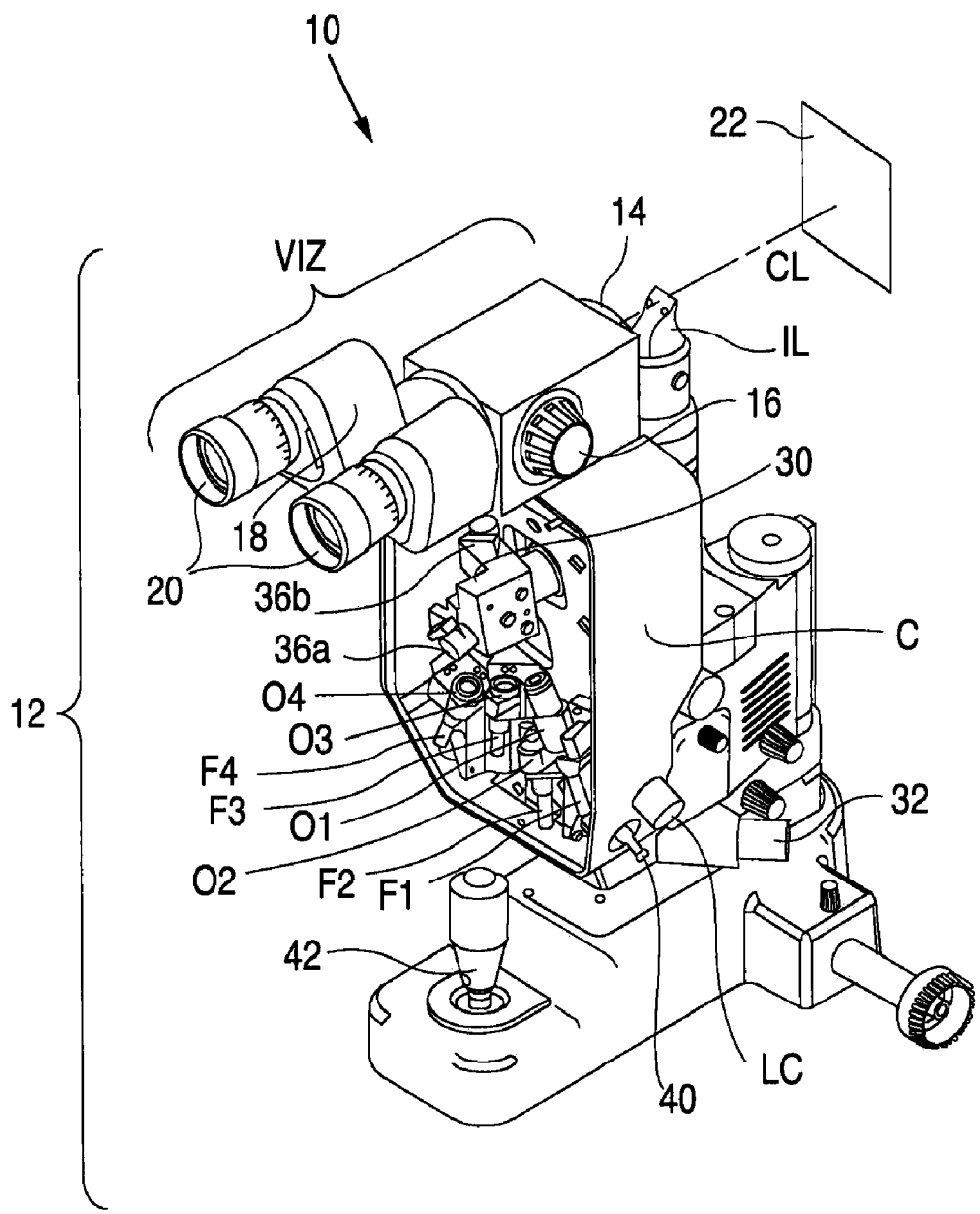
FIG. 1 is a diagram of a scanning photocoagulator consistent with one or more aspects of the present invention.

The innovations herein achieve adjustment of spot size and shape via techniques that differ from traditional approaches. According to certain aspects of an exemplary spot size adjustment embodiment discussed herein, multiple fibers may be used wherein some of the separate fibers can be of different size. Further, according to some of these aspects, the output of each fiber is directed to a dedicated optical path. Each of these optical paths can have a different magnification that results in a desired spot size at the treatment area. The multiple fiber and the separate output optical paths take advantage of the underutilized dynamic range of both the input and output galvanometric systems.

At the input to the fiber, a beam-deviating component such as a galvo system may be used for switching the delivered light on and off by directing the beam onto and off of the fiber face. Typically the fibers are small in diameter (<500 um) and the capability of the galvo scan coupled with an input focusing optical system allows for a beam movement much larger than the diameter of a single fiber. For example, the scan can be many millimeters in one direction. The galvo's range of capability is therefore underutilized for the sole purpose of switching. This underutilization can be tapped into by placing multiple fibers within the scan range of the galvo system, thereby enabling the selection of different size and shape fibers for delivery of light toward the output and subsequently toward the treatment area.

Similarly, at the output side of the fiber, the galvo system is also underutilized when used solely for the purpose of scanning the output of a single fiber onto the treatment area. This extra capability of the galvos can be similarly utilized by placing multiple fibers so that the one of several outputs can be selected for the scanning function by rotating one or more of the scanning mirrors such that it "selects" that fiber. By "selecting" a fiber (or fibers), light only from said fiber (or fibers) is allowed to traverse the entire optical system—ultimately reaching the therapeutic target tissue. Each of these fibers can be of different size and shape. Furthermore, the selection range is large enough to introduce separate optical systems at the output of each fiber. This allows for customizing the optical magnification for each path, creating flexibility for achieving a variety of spot sizes at the treatment plane.

According to some aspects consistent with the innovations herein, the choice to use a galvo technique for the switching and scanning functions also allows for the extra capability found in common galvo technology to be used to couple light into multiple fibers. Each fiber and the associated optical path to the treatment area can differ thereby adding versatility in choosing treatment parameters such as spot size and shape. Utilizing the galvos with the multiple fibers eliminates the need for a complex optical and mechanical system to achieve variable magnification such as found with turret and zoom systems. With the galvo-fiber system of the present invention, the burden with regard to economics, space, and performance tolerances is shared equitably across the major components.

Some aspects of the innovations herein are based on utilizing a plurality of optical fibers of different effective areas and/or numerical apertures as intermediate objects to provide adjustable beam diameters. An "intermediate object," as used herein, refers to any object in the optical path between the light source and the target. This approach deviates from traditional methods of using a single fixed source as the object of the optical system. Instead of using a single fixed source, fibers of different core diameters may be used to provide a relatively simple and robust fixed magnification optical system capable of generating different sizes of sharp spots on a target. Although the innovations described herein are described in the context of imaging, this is not a limitation of the invention. For example, a system of the invention may utilize a fiber bundle/array into which light is directed to a particular fiber.

The numerical aperture of an optical fiber (NA) is a well known property that is usually provided by the optical fiber manufacturer. For step-type fibers that have a core and a cladding, the rather simple calculation of NA can be made using the following formula:

$$NA=(n_1^2-n_2^2)^{1/2}$$

wherein $n_1$=the refractive index of the fiber core, and
$n_2$=the refractive index of the fiber cladding For an optical fiber without cladding (such as a bare core), the calculation is the same except the refractive index of air is substituted for that of the cladding in the above formula. For more complex optical fibers, such as a GRIN fiber having a refractive index that varies based upon radius, the determination is more complex.

The effective area of an optical fiber is the area of its light-transmitting material (e.g. its core) or the diameter of an aperture placed after the output end of the fiber. By varying the effective areas and/or the NAs of the optical fibers, the optical characteristics of the transmitted beam (i.e. divergence, spot size, shape, and diameter) can be varied.

FIG. 1 is a diagram of a scanning photocoagulator 10 consistent with embodiments of the invention. The photocoagulator 10 uses an ophthalmic slit lamp biomicroscope 12 that incorporates fibers of different core diameters. The ophthalmic slit lamp biomicroscope 12 includes microscope visualization components such as an objective lens 14, a magnification device 16, a binocular assembly 18, and eye pieces 20. These components constitute the imaging means with which a user (e.g., a physician) views the target (e.g., retina) along a centerline CL. The target is positioned at an image plane 22. The slit lamp biomicroscope 12 includes an integrated optical delivery system that has a fiber bundle 32 made of fiber inputs F1, F2, F3, F4 and a scanner 30. In this embodiment, the objective lens 14 is the final element in the array of optical elements.

The photocoagulator 10 includes integral controls for a micromanipulator 40, which in this case is coupled to a joystick 40. Typically, the micromanipulator 40 is directly joined to a fold mirror and the fold mirror is moved. The present invention, however, utilizes the scanner 30 and a set of moving mirrors 36a, 36b instead of a fold mirror that is directly joined to the micromanipulator 40. Moving the micromanipulator 40 causes the moving mirrors 36a, 36b to rotate, thus translating the beam on the target. This approach yields fine control of the disposition of the beam, limited by the resolution of the control electronics.

Light is brought to the photocoagulator 10 via the fiber bundle 32 from a light source (e.g., a laser source). Inside the slit lamp biomicroscope 12, the fibers F1, F2, F3, F4 of the fiber bundle 32 may be separated so that each fiber encounters one of the optical systems O1, O2, O3, O4. The output of each fiber and optical system, F1+O1, F2+O2, F3+O3, F4+O4, is pointed directly at the nearest of an orthogonal pair of moving mirrors 36a, 36b that are mounted on galvanometric scanners. The first mirror 36a redirects light to the second mirror 36b. Because the fibers F1, F2, F3, F4 are separated, the first mirror 36a is rotated into position to intercept the light from one of the fibers and direct it to the second mirror 36b. The fibers F1, F 2, F 3, F 4 are shown in more detail in FIG. 2 and FIG. 3.

Figure 6:
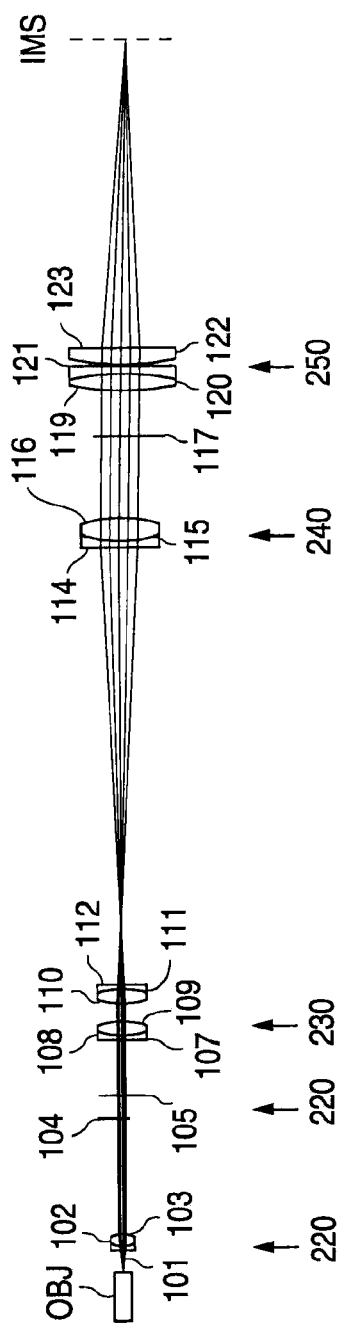
FIG. 6 is a schematic diagram of an exemplary output system for a selected fiber source with no aperture limitation consistent with one or more aspects of the present invention.

The scanner 30 may provide for a single beam spot to be delivered to the target, or a pattern of sequential beam spots. If a beam multiplier, such as a diffraction element (not shown) is added to the system, a plurality of beams may be delivered simultaneously (by spatial division of the optical beam) or a plurality of spots can be scanned sequentially (by temporal division of the optical beam). FIGS. 6 and 7 illustrate several embodiments of delivering sequential spots of light. Furthermore, a fiber optic splitter or switch may also be used in the body of the fiber optic to provide simultaneous and sequential beams, respectively.

Figure 2:
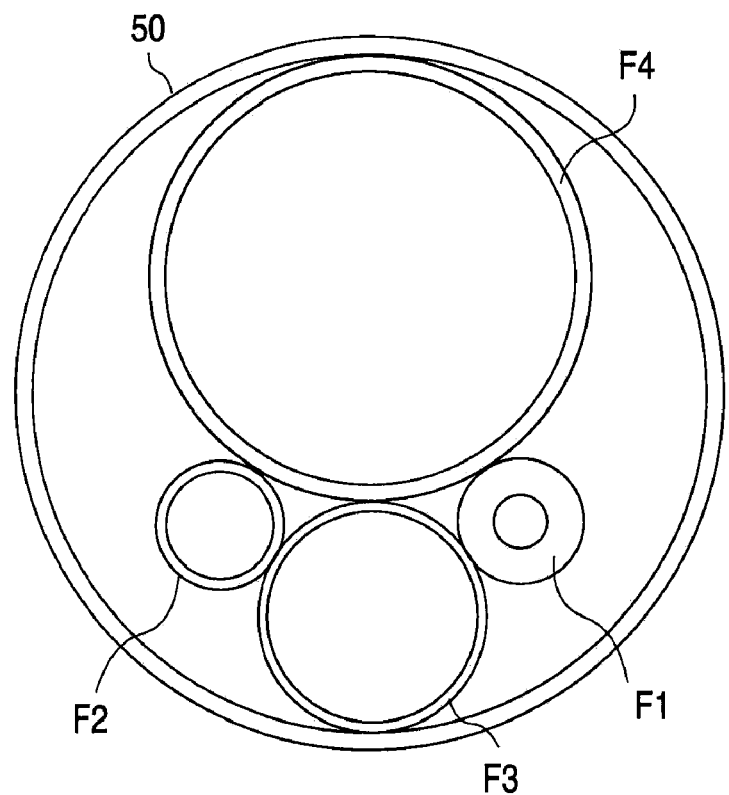
FIG. 2 is a cross-sectional diagram of the ferrule showing fibers F1, F2, F3, F4 in a bundled arrangement consistent with one or more aspects of the present invention.

FIG. 2 is a diagram of the ferrule 50 where the fibers F1, F2, F3, F4 are bundled together. While bundled fiber arrangements may be more compact and occupy less physical volume within overall optical systems, when the fibers are packed close together certain disadvantages apply. First, when bundled at the input side of the fiber unwanted illumination in unselected fibers and other stray light within the fibers can produce cross-talk in the fibers and at the target tissue. Therefore, bundled arrangements are more likely to deliver stray light from unselected fibers into the desired ejection point. Alternatively, unbundled configurations when used at the output of the fiber reduce this stray light because light from unselected fibers will not pass through the output side optical system and exit the system. Opaque sleeves may be used to surround the individual fibers. The sleeves would prevent light leakage between fibers along their length. The light sleeves would increase the overall diameter of the individual fibers and the sleeves would not prevent the inadvertent capture of stray light at the input face of an unintended fiber. Second, any optical system employing a bundled fiber system must necessarily contain one or both of additional system elements or more complicated arrangement of system elements to handle injection and ejection of light along multiple, adjacent beam paths. Therefore a bundled array typically requires a single fixed optical scheme that applies to all fibers within the bundle. This can occur at both the input and output sides of the fiber and for example increases the field of view requirement for the attending optical system. This added requirement for the optical systems can impose limitations upon otherwise dynamic system elements. Finally, unless the beam or beams are compensated, keeping the fibers bundled at the output will change the position of the ultimate disposition of light on the target. Such compensation may be achieved by using a scanner 30, as shown in the embodiment of FIG. 1, to make the correction for the relative displacement associated with each fiber of the bundle.

Figure 3A:
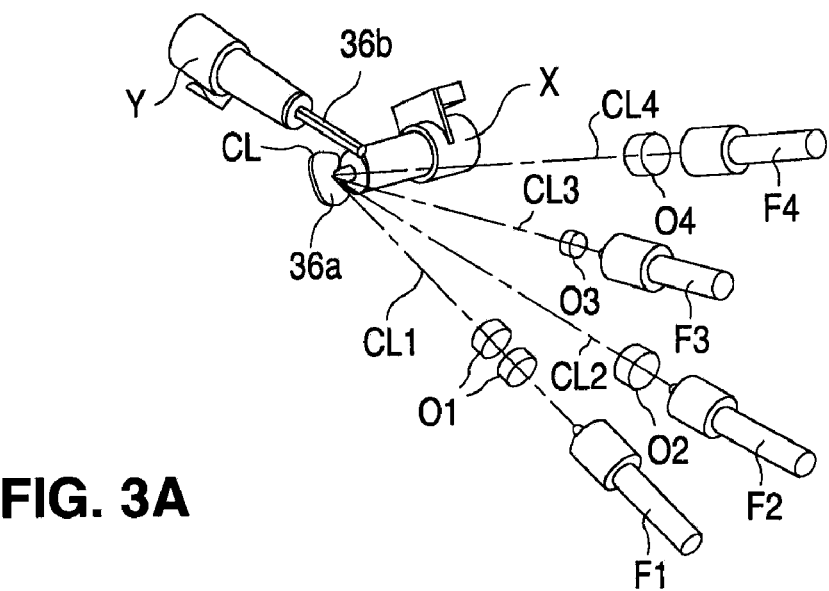
FIGS. 3A and 3B are diagrams of spaced-apart arrays of fibers and their respective optical systems consistent with one or more aspects of the present invention.
Figure 3B:
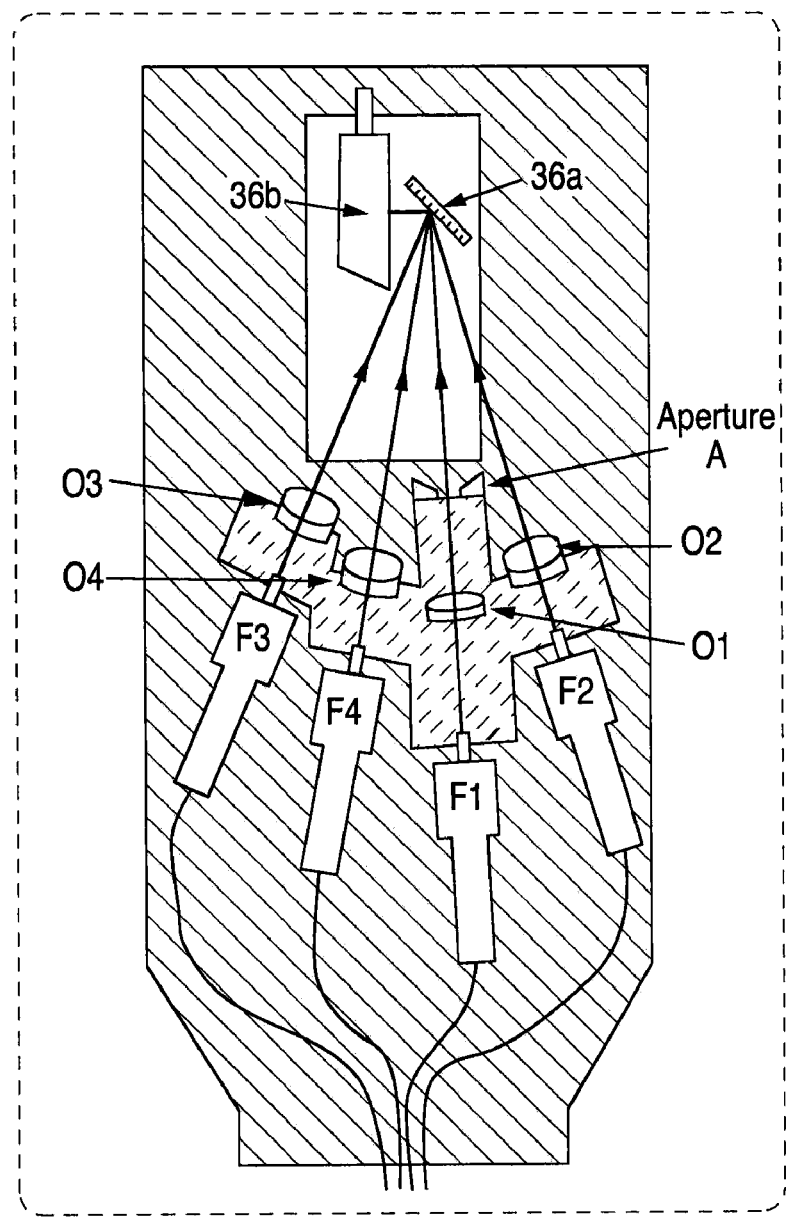

FIG. 3A is a diagram of the fibers F1, F2, F3, F4 and their respective optical systems O1, O2, O3, O4. Unlike in the embodiment of FIG. 2, where the fibers F1, F2, F3, F4 were bundled with a ferrule 50, the fibers are separated in this embodiment. The fibers F1, F2, F3, F4 and their respective optical systems O1, O2, O3, O4 are shown along with beam centerlines CL1, CL2, CL3, CL4 (denoted in dashed lines). This configuration has the benefit of reducing any stray light because each fiber (F1, F2, F3, F4) and its associated front end optical system (O1, O2, O3, O4) are independent and outside the field of view of the neighboring fibers. FIG. 3B is an alternative view of the separated fibers in a fan out arrangement at the output side of the fibers. The fibers are fanned out in the plane associated with the scan direction of the first galvo mirror, 36a. In this way, the output of a fiber can be selected by selecting the distinct galvo angle for that fiber. Scanning of the light emitting from this fiber can then ensue in one axis using the band of angles surrounding this selected angle for 36a and in the other axis using galvo 36b. Similarly, the configurations such as those of FIGS. 3A & 3B can be used on the input side to the fibers whereby the light from the source is reflected off the galvos and injected into the selected fiber. A X-Y scan or fan out configuration may be used here, as well.

Figure 4A:
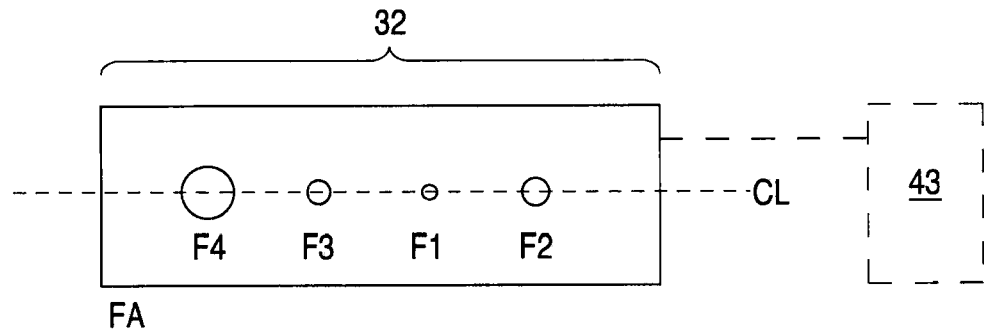
FIGS. 4A-4D are diagrams illustrating alternate embodiments of fiber injection arrays consistent with one or more aspects of the present invention.

FIG. 4A is a diagram illustrating a first exemplary input end of a fiber bundle 32, showing a linear injection array. The fibers F1, F2, F3, F4 are shown as having different diameters. In this particular embodiment, the fibers are arranged such that the smallest fiber F1 is in the middle of the array and two medium-sized fibers F2, F3 are next to the smallest fiber F1. The largest fiber F4 is separated from the smallest fiber F1 by one of the medium sized fibers F3. The line formed by the fibers lies along the scan direction of the galvo with the single optical system used for injecting the light into the fibers. The arrangement of the order of fiber sizes allows the optical system axis to be aligned to the smallest fiber, minimizing the requirements on the array's orientation for focusing and alignment off axis. Because the fiber size increases away from the center of the array, the centerline CL does not have to be precisely aligned to the plane described by the rotation of the mirror 60 in FIG. 5 below, while still allowing for injection into the individual fibers. In addition, the spatial separation of the fibers is large (many times the diameter of the individual fibers) thereby rejecting light from entering an unwanted fiber input.

Figure 4B:
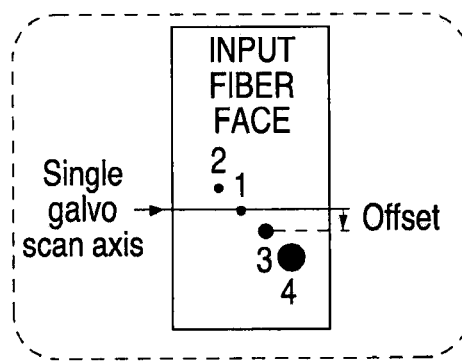

FIG. 4A also shows an optional and alternate technique for injecting light into the fibers. In this technique, a translation stage 43 may be used to move the fibers in relation to a fixed beam. Here, the translation stage 43 may move the fiber heads, for example, by means of mechanical or electromechanical devices, piezoelectric devices, galvos, motors, etc FIG. 4B is a diagram illustrating a second exemplary input end of a fiber bundle 32, showing an offset injection array. This offset configuration requires the use of two-dimensional scanning. Offset injection can provide several advantages over linear injection arrays. For example, as a result of the two-dimensional scanning techniques offset fiber injection ports eliminate or reduce entry of stray light into fibers because light entry requires the correct positioning of two independent scanners. In contrast, undesired light from one-dimensional scanning can impinge each port of a linear array as the scanned beam traverses the array from one side to the other. Offset arrays avoid this stray light as the injection ports are not subject to such scanning sweeps. Furthermore, the use of such offset arrays can employ a fiber bundle packed together at the output end and thus use a single common optical system thereafter. This enables reductions in the ultimate system costs and complexity.

A single fiber configuration would of course eliminate the problem of cross-talk of the multiple fiber system. But the single fiber system would restrict the fiber size to only one choice. The final spot size and the ability to vary the spot size would have to be accomplished via the subsequent output side optical system. This would have to be achieved by varying the magnification with a moving optical element. Examples are turret and zoom systems. These are complex opto-mechanical configurations. The multiple fiber configuration of the present invention allows for simple opto-mechanics while achieving the variation in delivered spot size. The stray light and cross talk issues associated with the multiple fibers can be sufficiently managed by leveraging the large dynamic range of scan movement associated with established galvanometric technology.

Figure 4C:
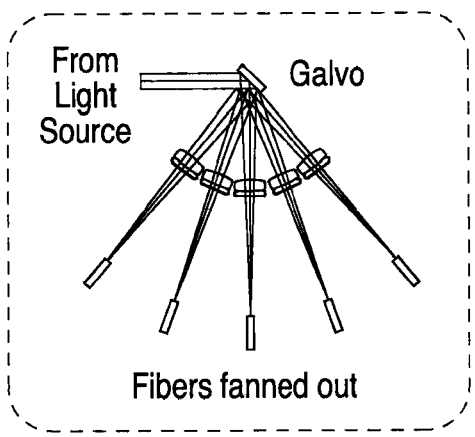

FIG. 4C is a diagram of another scheme for injecting light into the input side of the fibers. In this scheme, each of the fibers has an associated input optical system. The galvo position selects the appropriate fiber/optical combination path. FIG. 4C is input side analogue to the output side fan out configuration shown in FIG. 3A.

Figure 4D:
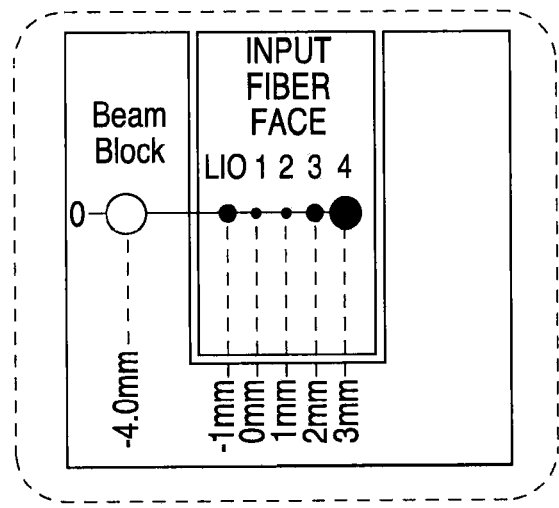

FIG. 4D is yet another representation of an input fiber face configuration. In this embodiment of the present invention, the fibers are arranged in a linear array much as in FIG. 4A but with an extra fiber, LIO. The output of this fiber can be used for another application not directly associated with the function of the remaining fibers. An example is that this fiber could be used as part of a laser indirect ophthalmoscope. Another feature of FIG. 4D is the inclusion of a specified beam block or beam dump. This beam block is for the purpose of absorbing the incident light and can be selected via the galvo. The beam block may be included as part of the fiber bundle face or could be located on a separate component. In FIG. 4D the beam block is located on the fiber bundle mounting mechanism. If interspersed along the array of fiber input faces, such beam blocks could be used in coordination with an adaptable system control scheme to eliminate the abovementioned difficulties associated with a one-dimensional fiber array of illuminating those fibers that lie between where the beam begins its scan, and where it ends. For example, the switching galvo may be used to direct the beam into a beam block immediately adjacent to the selected fiber, and thus switch into it without illuminating any other fibers.

Figure 5:
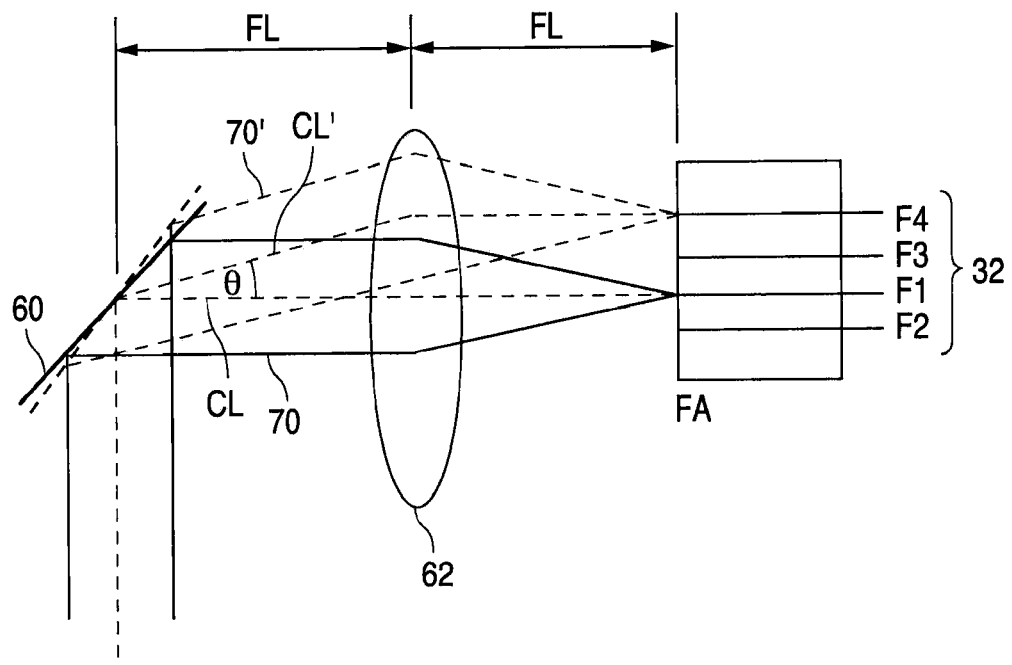
FIG. 5 is a schematic diagram of an exemplary scheme for injecting light into a specific fiber of the fiber bundle 32 consistent with one or more aspects of the present invention.

FIG. 5 is a schematic diagram of an exemplary scheme for injecting light into a specific fiber of the fiber bundle 32. A mirror 60 and an objective lens 62 are used to direct the optical beam toward a selected one of the fibers F1, F2, F3, F4. The moving mirror 60 is positioned at a first focal plane of a lens 62, and the fiber bundle 32 is positioned at a second focal plane of the lens 62. FIG. 5 shows two scenarios. Under one scenario where the mirror 60 is in the first position (shown by a thick solid line), the input beam is directed into a first fiber F1 as the optical beam 70 having a centerline CL. Under another scenario, the mirror 60 is rotated to a second position shown by a dashed line. With the mirror 60 in the second position, the input beam is directed into a fourth fiber F4 as the optical beam 70' having a centerline CL'. The mirror 60 may be rotated by θ/2 to redirect the optical beam 70' at an angle θ relative to the optical beam 70, measured between the centerlines CL and CL'. Thus, rotating the mirror 60 causes the optical beam to be translated on the image plane (not shown) of the lens 62.

This arrangement creates a telecentric condition at the input to the fiber face, and the input to each fiber is normal. In such a telecentric configuration, CL and CL' are parallel at the input to the fiber face. Thus, the rotation of the mirror 60 does not cause the input beam to enter the selected fiber normally. An angled optical beam may not be well-received by the fiber, as it may be outside of the fiber's intrinsic numerical aperture. To accommodate this, the fiber bundle 32 may be made to have input faces of its constituent fibers arranged in an arc instead of in a linear fashion as in FIG. 4. Although the mirror 60 is used in this embodiment, the mirror 60 may be replaced by any alternative element that redirects the optical beam 70, such as another lens element, and translated laterally to achieve a substantially same effect.

A mirror mounted on a galvanometric scanner allows for relatively fast switching, and may be used for an optical switch of the type disclosed in the copending U.S. patent application Ser. No. 11/523,159 titled "Optical Switch."

Different spot shapes can be achieved by the choice of the fiber cross-sectional geometry. For example, when the fiber face is imaged into the target plane, the shape is preserved. The common circular cross sectional fiber geometry is circular, but other geometries such as ellipses, rectangles, and polygons also apply.

Figure 7A:
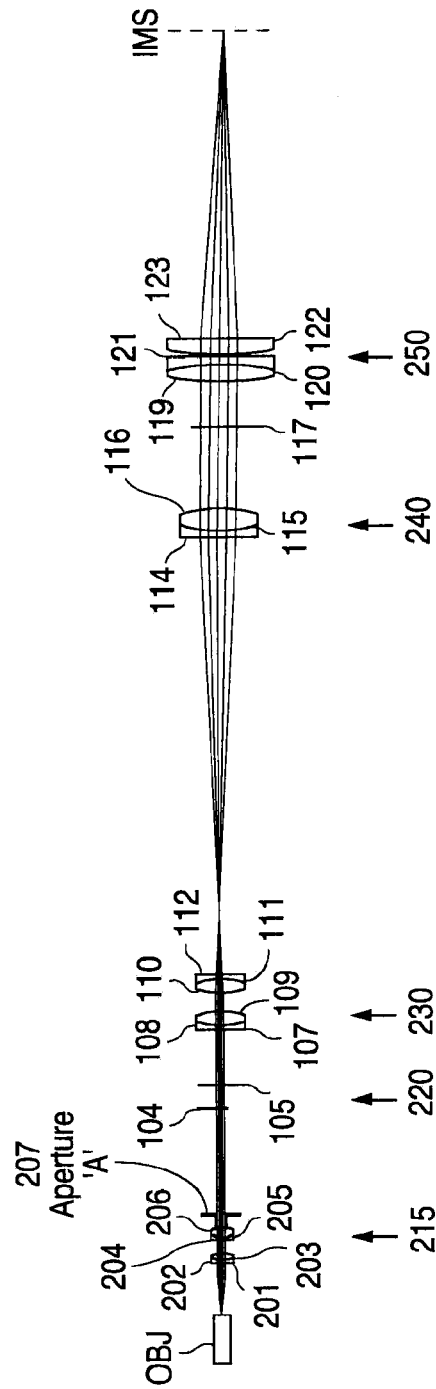
FIGS. 7A and 7B are schematic diagrams of an alternate embodiment of an exemplary output system for a selected fiber source having aperture limitation consistent with one or more aspects of the present invention.
Figure 7B:
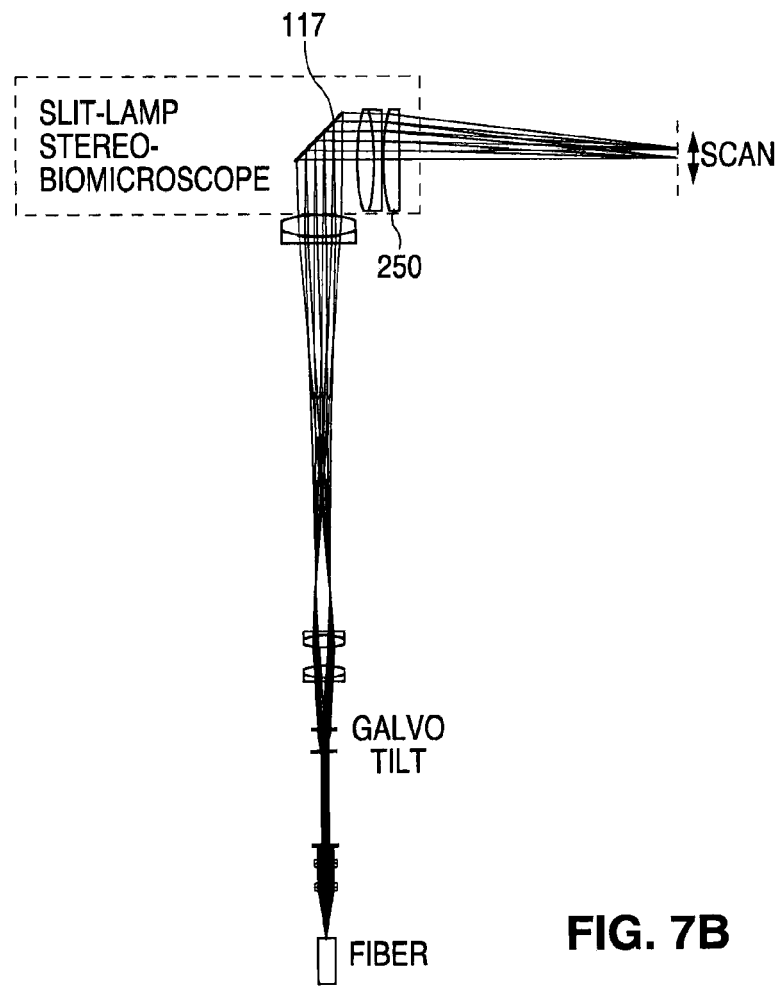

FIGS. 6, 7A and 7B illustrate exemplary fixed magnification optical systems, e.g., at fiber ejection points. Such optical system may be used, for example, at a constant numerical aperture in the target space across all fibers and produce spot sizes that are proportional to the fiber core diameter. Maintaining near constant NA as spot size is varied provides increased safety for any intermediate structures because the minimum spot size is at the target. Normally larger spots are associated with smaller NA beams and the associate soft focus and large latitude of beam waist location thereby subjecting nearby structure to the target to potentially damaging high fluences. Another benefit of embodiments of the present invention is that all of the fibers may operate at the same numerical aperture at the fiber output, regardless of core diameter, and therefore produce the same spot size on the target. FIGS. 6 and 7A are schematic raytraces showing two approaches for delivering sequential spots of light, a straight-through approach and an aperture-limited approach, respectively. In the straight-through optical scheme of FIG. 6, the magnification level from fiber face to the target area is approximately 2 and the delivered numerical aperture in target space is 0.06. The delivered numerical aperture in target space need not be the intrinsic numerical aperture of the fiber, but may be altered by using optical magnification, where the magnification is set at a non-unitary value, such as is shown in FIG. 6. It is known in the art that a fiber may be made to largely preserve the input launch numerical aperture if $(NA)_i > 0.10$. In FIG. 6, then, the following optical prescription applies.

TABLE 1

| SURFACE | RADIUS | THICKNESS | APERTURE RADIUS | MATERIAL |
|---|---|---|---|---|
| OBJ | — | 8.295000 | 0.025000 | AIR |
| 101 | 26.180000 | 2.000000 | 4.500000 | SF57 |
| 102 | 7.010000 | 5.000000 | 4.500000 | BAFN10 |
| 103 | −8.370000 | 45.000000 | 4.500000 | AIR |
| 104 | — | 9.500000 | 1.459960 | AIR |
| 105 | — | 21.00000 | 1.524664 | AIR |
| 107 | 226.770000 | 2.000000 | 9.000000 | SF10 |
| 108 | 26.240000 | 3.850000 | 9.000000 | BAFN10 |
| 109 | −42.510000 | 7.800000 | 9.000000 | AIR |
| 110 | 27.120000 | 5.000000 | 9.000000 | SSKN8 |
| 111 | −25.660000 | 2.300000 | 9.000000 | SF10 |
| 112 | −538.700000 | 20.770000 | 9.000000 | AIR |
| 113 | — | 144.550000 | 0.066180 | AIR |
| 114 | 195.870000 | 2.600000 | 15.000000 | SF5 |
| 115 | 65.570000 | 8.100000 | 15.000000 | BK7 |
| 116 | −91.310000 | 33.000000 | 15.000000 | AIR |
| 117 | — | 17.000000 | 10.000000 | AIR |
| 119 | 160.700000 | 6.000000 | 21.000000 | SK11 |
| 120 | −97.560000 | 3.500000 | 21.000000 | SF3 |
| 121 | −986.500000 | 0.100000 | 21.000000 | AIR |
| 122 | 93.920000 | 6.000000 | 21.000000 | SK16 |
| 123 | 709.920000 | 116.875000 | 21.000000 | AIR |
| IMS | — | — | 0.055914 | |

The optical surfaces in FIG. 6 are denoted by surface numbers as also indicated in the prescription in Table 1. The following functional description groups these surfaces into elements to facilitate clarity with regard to the explanation. The OBJ surface represents the output face of a single fiber and acts as the object of the optical train. This object plane is imaged with magnification into the final image plane denoted by IMS in the figure. Element 210 consisting of surfaces 101, 102, & 103 is the front end of the optical system. Element 210 is dedicated to the output of a single fiber and is generally split off from the other optical fiber channels and their associate dedicated front end optical systems. For example, element 210 is the part of the optical train that is in the fan-out before the beam is combined via the galvo with the common optical elements. Element 210 is therefore the optical component that allows for the differences in magnification between the optical channels associated fro example with each fiber in the fiber bundle. Said element 210 could be placed in the position to collimate the optical beam emitted from the fiber. The equivalent optical group in-the other paths can be set to the same conjugate position i.e. collimated, so that all the paths are compatible with the common optical beam and share a common working distance to the IMS plane. The common optical train is denoted by elements 220, 230, 240, & 250 and is described below. The overall magnification of the beam train can therefore be set by choosing the appropriate focal length for element 210. Element 210 is followed by the galvo group 220 denoted by surfaces 104 and 105. Galvo 104 selects the individual fiber from which the light will be directed into the common optical train. Galvo 104 also provides scanning in the IMS plane. A second galvo, 105, is used to enable two-dimensional scanning at the IMS plane. Galvo 105 can also be used to select the output of a specific fiber. Group 230 represented by surfaces 107, 108, 109, 110, 111, 112 is the scan optical grouping. This group 230 accepts the light immediately after the scanning element 220 and establishes an intermediate image plane following near to surface 112. To establish a compact design, element 230 operates at the high field of view and at a relatively fast f-number as dictated by the scan and galvo parameters such as extent of the scan and clear aperture of the galvo mirrors. Additionally, the optical parameters for element 230 are selected to control the scan angle at IMS. It is commonly required for a substantially telecentric scan condition at IMS. This requires the optical group, 230, to place the image plane of the galvo positions near or at the front focal length of the relay group represented by elements 240 & 250. In order to control aberration, element 230 may be a complex compound optical element such as the two lens design shown. Elements 240 & 250 consisting of surfaces 114, 115, 116, 119, 120, 121, 122, 123 comprise an optical portion of the system that relays the aforementioned intermediate image into the final image plane, IMS. Element 250 is the objective lens of the slit-lamp. This objective lens is shared with the visual stereo-biomicroscope function. As such, this lens is commonly determined by the parameters as set forth by the stereo-biomicroscope requirements. For example, the objective lens of the slit-lamp is commonly designed to operate as an infinity corrected, fixed focal length optic with an working distance on the order of 120 mm. Element 240 is therefore used to adapt the intermediate image to work with these existing constraints so that the scan requirements and spot size requirements at the image plane IMS are satisfied. Surface 117 represents a fold mirror or some equivalent mechanism to combine the scan light path with the slit-lamp biomicroscope visual path.

FIG. 7A is a schematic diagram of an aperture-limited embodiment where different fibers F1, F2, F3, F4 use different optical systems O1, O2, O3, O4 and thus have independent control of the respective numerical apertures in the target space. This embodiment is advantageous in situations where it is desired to use a fiber's intrinsic numerical aperture, but alter it because of the etendue of the: target or source or some other limiting feature or set of features. An example is found in a common slit lamp configuration. The maximum practical NA at target space of NA=0.06 is set by the objective of the slit lamp for unobscured use. A common minimum spot at the target is 50 um. The product of NA (0.06) and spot diameter (50 um) is therefore set. The minimum practical NA for fibers is approximately NA=0.12. It is therefore throughput efficient to have a magnification of at least a factor of 2 from fiber face to target. This may conflict with minimum spot size requirements. For example, to deliver a 50 um spot at the target with a 2× magnification would require a fiber with diameter 25 um at NA=0.12. Launching into such a fiber with a high power multimode laser beam would be inefficient. Therefore tradeoffs arise as to how to best match etendue limiting features in the most efficient manner. An example of such a trade-off is illustrated in FIG. 7A, where a 50-μm core diameter fiber (e.g., fiber F1 in FIGS. 1, 3, and 4) is used at its intrinsic numerical aperture of 0.12, and delivered at a magnification of unity to the target to therefore yield a spot size of 50 um. An aperture A is inserted to reduce its effective numerical aperture at the target plane to 0.06. Therefore the loss in the beam is controlled by the aperture instead of the downstream slit lamp constraints. Further, the high power multimode laser is efficiently coupled into 50 um fiber at intrinsic NA=0.12. The aperture location is ideally chosen to take advantage of irradiance distributions and to minimize loss. For example the aperture location can be at a plane where the irradiance distribution is essentially Gaussian as in FIG. 7. Alternatively, aperture A may also be placed directly at the output face of the fiber in some embodiments. However, at this location, there is maximum power density and a uniform intensity distribution. As such, the aperture would need to survive in extreme conditions and would attenuate the beam geometrically according to the following relationship:

$$P_t = P_0 (D_{aperture}/D_{fiber})^2$$

where $P_t$=transmitted power,
$P_0$=power delivered by the fiber,
$D_{fiber}$=fiber diameter, and
$D_{aperture}$=aperture diameter.

Using tapered fibers is another strategy for adjusting spot size or numerical aperture at the input or output of the fiber. In tapered configurations where the cross-sectional dimensions are reduced as a function of length, the beam product and therefore the etendue is preserved because as the diameter of the waveguide or fiber is reduced, correspondingly the NA increases. Tapering the input of the fiber differentially with regard to the output of the fiber, for example, may allow for more compatible or simplified design of the input and output optical systems. An aperture or some other set of features that limit the spot size or NA or both may be needed to reliably control the transmission loss in a system where the etendue of the fiber is greater than the etendue of the target and/or light source.

In the case of a 50 μm fiber and a 25 μm aperture, $P_t = 0.25 P_0$. Placing the aperture in the far field as in FIG. 7A where the beam has a nominally Gaussian intensity distribution, however, allows for the numerical aperture to be reduced, and the transmitted power to be higher than otherwise attainable. For example, a 50-μm fiber operating at a numerical aperture of 0.12 may be restricted to a numerical aperture of 0.06, as shown in FIG. 7A, while transmitting close to 60% of the light delivered by the fiber. The optical prescription of Table 2 applies to this configuration.

TABLE 2

| SURFACE | RADIUS | THICKNESS | APERTURE RADIUS | MATERIAL |
|---|---|---|---|---|
| OBJ | — | 19.400000 | 0.025000 | AIR |
| 201 | 46.140000 | 1.500000 | 4.500000 | SF5 |
| 202 | 15.980000 | 2.500000 | 4.500000 | BK7 |
| 203 | −22.160000 | 5.000000 | 4.500000 | AIR |
| 204 | 78.350000 | 1.500000 | 4.500000 | SF5 |
| 205 | 26.330000 | 3.500000 | 4.500000 | BK7 |
| 206 | −36.510000 | 5.000000 | 4.500000 | AIR |
| 207 | — | 40.000000 | 1.500000 | AIR |
| 104 | — | 9.500000 | 2.999965 | AIR |
| 105 | — | 21.000000 | 3.009884 | AIR |
| 107 | 226.770000 | 2.000000 | 9.000000 | SF10 |
| 108 | 26.240000 | 3.850000 | 9.000000 | BAFN10 |
| 109 | −42.510000 | 7.800000 | 9.000000 | AIR |
| 110 | 27.120000 | 5.000000 | 9.000000 | SSKN8 |
| 111 | −25.660000 | 2.300000 | 9.000000 | SF10 |
| 112 | −538.700000 | 20.770000 | 9.000000 | AIR |
| 113 | — | 144.550000 | 0.030001 | AIR |
| 114 | 195.870000 | 2.600000 | 15.000000 | SF5 |
| 115 | 65.570000 | 8.100000 | 15.000000 | BK7 |
| 116 | −91.310000 | 33.000000 | 15.000000 | AIR |
| 117 | — | 17.000000 | 10.000000 | AIR |
| 119 | 160.700000 | 6.000000 | 21.000000 | SK11 |
| 120 | −97.560000 | 3.500000 | 21.000000 | SF3 |
| 121 | −986.500000 | 0.100000 | 21.000000 | AIR |
| 122 | 93.920000 | 6.000000 | 21.000000 | SK16 |
| 123 | 709.920000 | 116.875000 | 21.000000 | AIR |
| IMS | — | — | 0.027426 | |

In FIG. 7A, elements and surfaces common to previous Figures such as FIG. 6 have been denoted with the same call out numbers. The common optical path represented by elements 220, 230, 240, & 250 operate as described previously. Element 215 as represented by surfaces 201, 202, 203, 204, 205, & 206 depicts the front end optical system designated for the specified fiber output. For example, element 215 may be the front end optical system O1 dedicated to fiber F1. Element 215 establishes the overall optical magnification and enables the ability to create a different magnification from to the optical paths associated with the other fibers. Therein, element 215 along with the rest of the optical train as represented by elements 220, 230, 240 & 250 may, for example, set an overall magnification of near unity using a fiber with a core diameter of 50 um and a fiber intrinsic NA=0.12. The unity magnification would result in a 50 um spot diameter at the image plane IMS and a corresponding NA=0.12 at IMS. Normally, a slit-lamp biomicroscope will not allow a NA=0.12 beam to exit the objective, 250, without significant clipping of the beam and therefore uncontrolled attenuation of the beam transmission. The aperture 'A' as denoted by 207 in FIG. 7A depicts an aperture placed in the beam in order to limit the NA in the IMS plane. The placement of 207 as shown is chosen to be located at a plane with a substantially Gaussian irradiance distribution. This location minimizes transmission loss while controlling output NA in a controlled manner. The diameter of aperture A, 207 determines the final NA at IMS.

FIG. 7B depicts the optical train of FIG. 7A folded into the slit-lamp stereo-biomicroscope. In FIG. 7B a one-dimensional galvo mirror tilt and the resulting scan are shown. Fold mirror, 117 is shown combining the scanning beam into the slit-lamp visual field of view de-centered from the optical axis of the objective, 250. Alternative combining geometries can be used. These include placement of the fold 117 after the objective 250 and use of a dichroic or partial reflecting beamsplitter to combine on or off the optical axis of objective.

Figure 8:
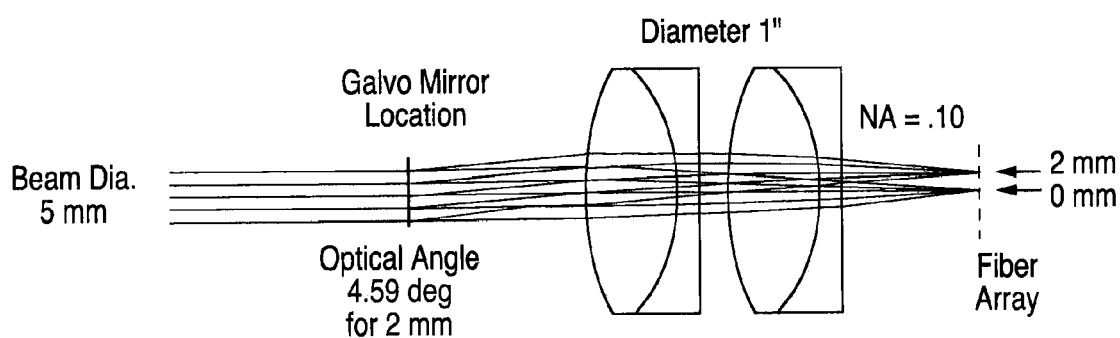
FIG. 8 is a diagram illustrating alignment of an optical beam centerline with the plane of the mirror of the configuration of FIG. 5 consistent with one or more aspects of the present invention.
Figure 13:
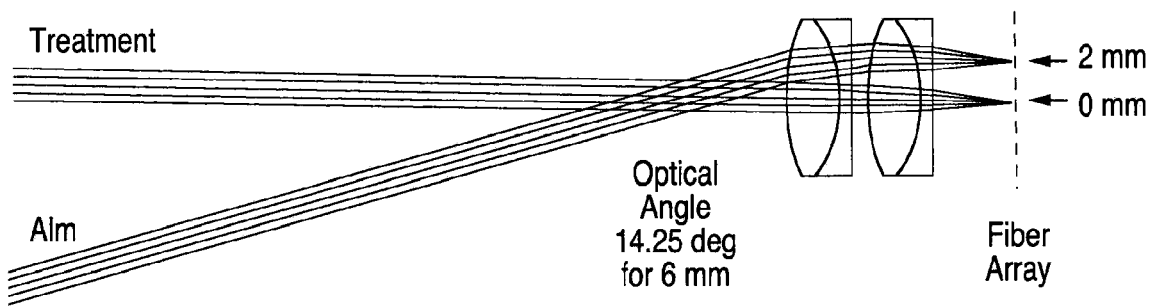
FIG. 13 is a diagram illustrating how multiple light sources can be combined into the fiber bundle consistent with one or more aspects of the present invention.

FIG. 8 is a diagram of a configuration at the input side of the fiber illustrating that the centerline CL of the optical beam does not need to be precisely aligned to the plane of the mirror 60 in FIG. 5. Even without the precise alignment, the optical beam is injected into the individual fibers with satisfactory results. Other techniques of using moving elements to inject light into arrays of optical fibers are set forth in FIGS. 9A-12B. While described here in the context of an optical switch, use of these techniques in connection with a variety of other optical systems, elements and components is consistent with the present invention. Further, FIG. 13 illustrates a photomedical system 100 and optical switch 310 suitable for implementing the fiber optic/light injection features and functionality described above.

FIGS. 9A and 9B show a configuration of an optical switch 310 wherein a lens L1 is located on the output side 322 of the aperture element 314. In FIG. 9A, the moving mirror M1 is at an angle such that the optical beam 316 is reflected toward the light-transmitting portion 318 of the aperture element 314. More than a critical fraction (e.g., substantially all) of the optical beam 316 reaches the lens L1, which focuses the optical beam 316 into the input end of an optical fiber 342. The state in FIG. 9A represents the pulse being "on." If the moving mirror M1 rotates, the optical beam 316 is reflected so that some of it is directed toward the light-transmitting portion 318 but the rest of it is incident on the light-blocking portion 319, as shown in FIG. 9B. Under these conditions, the amount of optical beam 316 that enters the optical fiber 342 is significantly reduced (or eliminated) compared to the conditions in FIG. 9A. If less than the critical fraction of the optical beam is incident on the light-transmitting portion 318, the pulse is in an "off" state. The light is repeatedly turned on and off (i.e. pulse generation) by changing the position of the moving mirror M1. The pulse being "on" or "off" is described as viewed from the output side 322 of the aperture element 314. When used with optical fibers, the aperture element 314 could be an element separate from optical fiber 342, or could be incorporated as part of the optical connector at the end of the optical fiber 314, such as is shown in FIGS. 10A and 10B. The transmitting portion may also be the core of the optical fiber itself. When the fiber is used as the aperture, it must be noted that it accepts light only in its core, and only at a certain numerical aperture (NA). In this way, optical beam 316 may be switched on and off by moving it on the core, and/or by changing its incident angle.

FIGS. 10A and 10B show a configuration of the optical switch 310 wherein the lens L1 is located on the input side 320 of the aperture element 314, between the moving mirror M1 and the aperture element 314. In FIG. 10A, the lens L1 focuses the optical beam 316 from the moving mirror M1 on the light-transmitting portion 318 of the aperture element 314. The optical fiber 342 is positioned close to the aperture element 314 so that substantially all of the optical beam 316 is coupled into the optical fiber 342. The state in FIG. 10A represents the pulse being "on." If the moving mirror M1 rotates, the optical beam 316 is directed to the lens L1 off-center so that the lens L1 focuses the beam on a light-blocking portion 319 of the aperture element 314, as shown in FIG. 10B. Under these conditions, the amount of optical beam 316 that enters the fiber unit 342 is significantly reduced (or eliminated) compared to the conditions in FIG. 10A. If less than the critical fraction of the optical beam is incident on the light-transmitting portion 318, then the pulse is in an "off" state. The light is repeatedly turned on and off (i.e. pulse generation) by changing the position of the moving mirror M1.

Figure 11A:
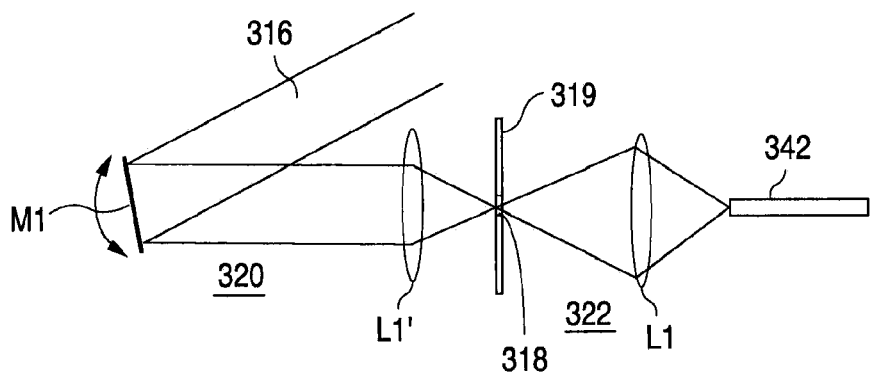
Figure 11B:
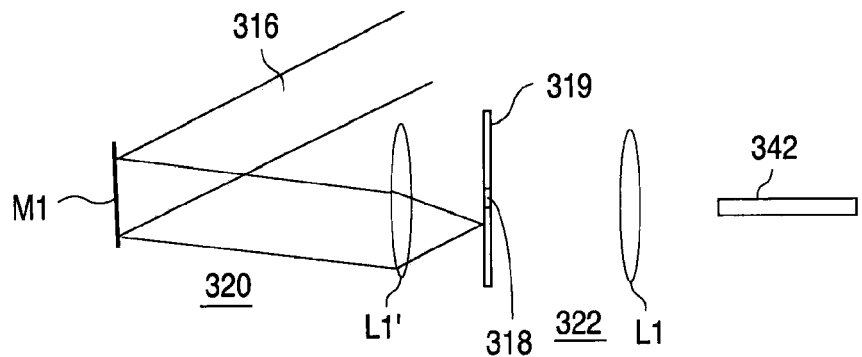

FIGS. 11A and 11B show a configuration of the optical switch 310 wherein the lens L1 is located on the output side 322 of the aperture element 314 and a lens L1' is located on the input side 320 between the moving mirror M1 and the aperture element 314. In FIG. 1A, the moving mirror M1 is at an angle such that the lens L1' focuses the optical beam 316 onto the light-transmitting portion 318 of the aperture element 314. The lens L1 is positioned such that its focal point lies in the light-transmitting portion 318 of the aperture element 14 and coincides with the focal point of the lens L1'. The lens L1 then focuses the optical beam 316 that passed through the aperture element 314 into the optical fiber 342. Since more than a critical fraction of the optical beam 316 is incident on the light-transmitting portion 318, the state in FIG. 11A represents the pulse being "on." If the moving mirror M1 is rotated, the lens L1' focuses the optical beam 316 on the light-blocking portion 319, as shown in FIG. 11B. Under these conditions, less than the critical fraction of the optical beam passes through the aperture element 314, and the pulse is in an "off" state. The light is repeatedly turned on and off (i.e. pulse generation) by changing the position of the moving mirror MI. With the use of an extra lens L1' on the input side 320, the light-transmitting portion 318 of the aperture element 314 may be made much smaller than in the case where there is no lens L1' (e.g., in FIG. 9A and FIG. 9B) because the light is focused to a very small diameter at the aperture element 314 while its angular velocity is increased. This combination yields amplified switching speeds.

Figure 12:
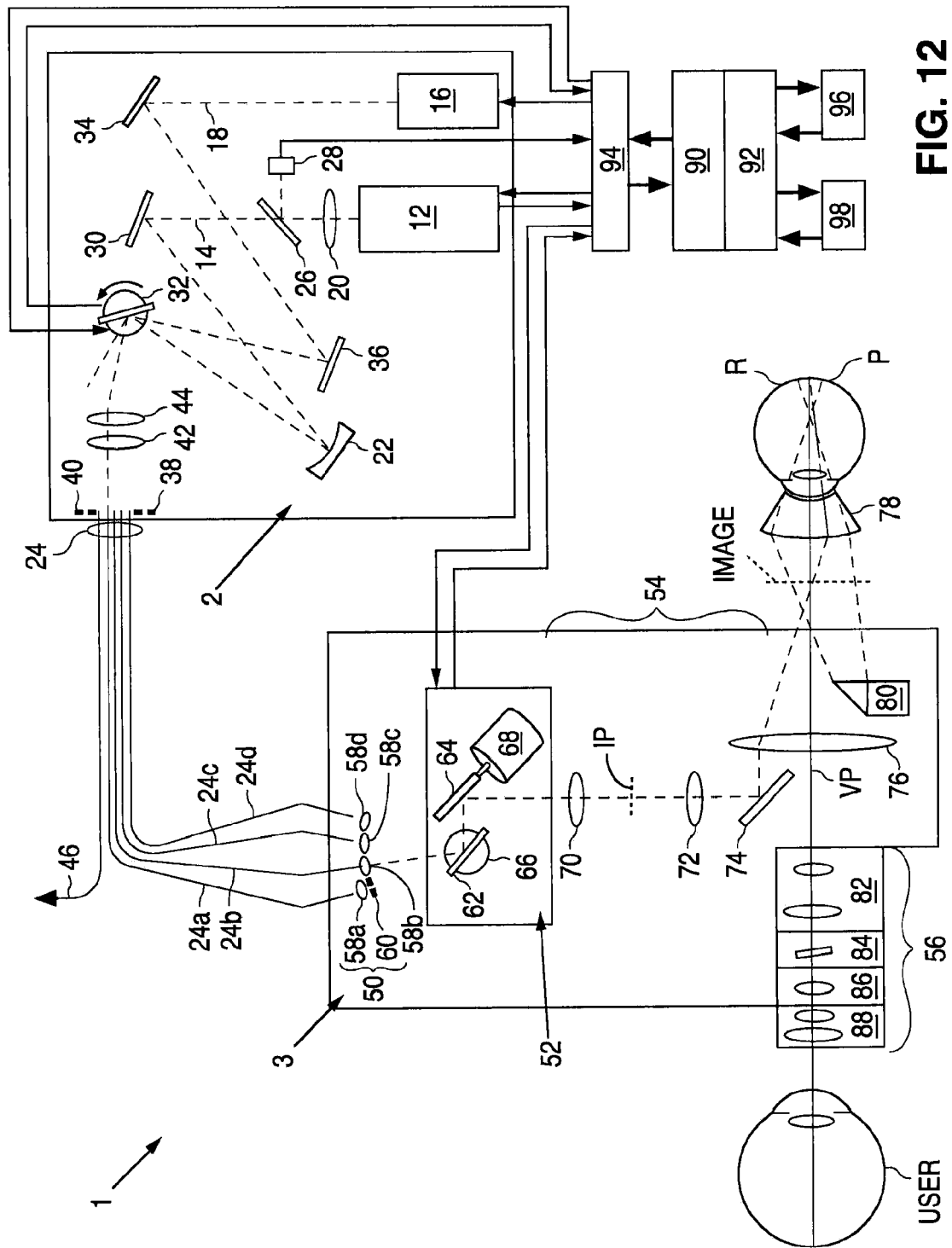
FIG. 12 is a schematic diagram of a photomedical system consistent with one or more aspects of the present invention.

FIG. 12 depicts an ophthalmic slit lamp based scanning photocoagulator 1, which is a non-limiting example of a photocoagulation system for creating and projecting aiming and/or treatment patterns of spots onto a patient's retina R. System 1 includes a light source assembly 2 and a slit lamp assembly 3.

The light source assembly 2 includes a treatment light source 12 for generating an optical beam of treatment light 14, and an aiming light source 16 for generating an optical beam of aiming light 180. Treatment beam 14 from treatment light source 12 is first conditioned by lens 20, which is used in conjunction with a curved mirror 22 to prepare treatment beam 14 for input into an optical fiber bundle 24. After encountering lens 20, treatment beam 14 is sampled by partially reflecting mirror 26. The light reflected from mirror 26 is used as an input for a photodiode 28 that monitors the output power of treatment beam 14, assuring that the light source 12 is operating at the desired power. A mirror 131 is used to steer treatment beam 14 onto mirror 22, which in turn directs treatment beam 14 onto moving mirror 132. Aiming beam 180 from aiming light source 16 is directed onto moving mirror 132 via mirrors 34 and 136.

Moving mirror 132 is preferably mounted on a galvanometric scanner (but could also be moved by piezo actuators or other well know optic moving devices), and moves to selectively direct treatment and aiming beams 14, 180 to one of the optical fibers 24a, 24b, 24c, 24d of optical fiber bundle 24 at any given time, where lenses 42, 44 focus the treatment and aiming beams 14, 180 into the selected optical fiber(s). Preferably, moving mirror 132 is spaced one focal length away from lens 20 to provide for a telecentric scan condition (thus allowing for the injection of treatment beam 14 into all the optical fibers 24a-24d on parallel paths, which preserves the launch numerical aperture across the optical fiber bundle 24). Adjacent to the optical fibers 24a-24d are beam dumps 38, 140, which provide convenient locations to "park" the treatment beam 14. Optical fibers 24a-24d are used to deliver the treatment and aiming beams 14, 180 from the light source assembly 2 to the slit lamp assembly 3. An additional optical fiber 46 may be used to direct the treatment and/or aiming beams 14, 180 to the patient via other means such as an endoprobe or laser indirect ophthalmoscope (not shown).

Slit lamp assembly 3 includes an optical fiber input 150 (for receiving optical fibers 24a-24d), a scanner assembly 52, a delivery assembly 54, and a binocular viewing assembly 56. The optical fiber input 150 preferably includes a unique optical conditioning system for each of the optical fibers 24a-24d, so that each optical fiber can produce a specific (and preferably unique) spot size at the image plane IP of the slit lamp assembly 3. For example, light from optical fiber 24a first encounters a lens 58a that collimates the light, followed by an aperture 60 that serves to reduce the effective numerical aperture by obscuring all but the central portion of the light beam. Light from optical fibers 24b through 24d first encounter lenses 58b through 58d, respectively. Lenses 58b-58d are preferably configured to create different spot sizes at the image plane IP, and subsequently at the target tissue (retina R). In the illustrated example, optical fibers 24a and 24b have the same core diameter, but are made to create different spot sizes by using different lenses 58a and 58b. Optical fibers 24c and 24d have different core diameters. It is preferable (but not necessary) that all optical fibers deliver light with the same numerical aperture. Therefore, to keep the operating numerical apertures identical for these different channels, aperture 60 is used to counteract the change in optical power of lens 58a relative to lenses 58b, 58c, 58d.

The optical output of each optical fiber 24a-24d after conditioning by the associated optical systems (e.g. lenses 58a-58d, aperture 60, etc.) is directed to the scanner assembly 52, which includes two movable mirrors 162, 64 mounted to two galvanometers 66, 68 (although any well known optic moving device such as piezo actuators could be used). Mirrors 162, 64 are configured to rotate in two orthogonal axes to scan (i.e. translate) the incoming light to form any desired pattern P. Mirror 162 may be rotated to redirect the light from any given one of the fibers 24a-24d into the remainder of slit lamp assembly 3, thus acting to "select" the output from that optical fiber while prohibiting any light from the other optical fibers to continue through the entire slit lamp assembly 3. Because the output ends of optical fibers 24a-24d are not coincident, mirror 162 must be rotated into position to intercept the light from the desired optical fiber and transmit that light to mirror 64, which can further move the light in an orthogonal axis. This configuration has the added benefit of preventing any stray light that may be delivered by the non-selected optical fibers from exiting the system. In FIG. 1, optical fiber 24b is shown as the selected fiber, where the output of this fiber is scanned by mirrors 162, 64 to create a scanned pattern of light that travels through the rest of the system.

The scanned pattern of light P (which originates from treatment light source 12 and/or aiming light source 14) leaving the scanner assembly 52 passes through the delivery assembly 54, which includes lens 170 (for creating the intermediate scanned pattern at image plane IP), lens 72 (for conditioning the light pattern for focusing into the eye), mirror 74 (for directing the light pattern toward the target eye tissue), lens 76 (preferably an infinity-corrected microscope objective lens) and lens 78 (preferably a contact lens that provides final focusing of the pattern of light P onto the target eye tissue such as the retina R). Illumination source 80 (such as a halogen light bulb) is used to illuminate the target eye tissue R so that the physician can visualize the target eye tissue.

The user (i.e. physician) views the target eye tissue R directly via the binocular viewing assembly 56, which includes magnification optics 82 (e.g. one or more lenses used to magnify the image of the target eye tissue, and preferably in an adjustable manner), an eye safety filter 84 (which prevents potentially harmful levels of light from reaching the user's eye, and which may be color-balanced to provide for a photopically neutral transmission), optics 86, and eyepieces 88.

Pattern P of light is ultimately created on the retina of a patient R using optical beams 14, 180 from treatment light source 12 and aiming light source 16 under the control of control electronics 90 and central processing unit (CPU) 92. Control electronics 90 (e.g. field programmable gate array, etc.) and CPU 92 (e.g. a dedicated microprocessor, a stand-alone computer, etc.) are connected to various components of the system by an input/output device 94 for monitoring and/or controlling those components. For example, control electronics 90 and/or CPU 92 monitor photodiode 28 (to ensure treatment beam 14 is generated at the desired power level), operate the light sources 12, 16 (turn on/off, set power output level, etc.), operate mirror 132 (to select which optical fiber will be used for treatment and/or aiming beams 14, 180), and control the orientations of galvanometric scanners 66, 68 to produce the desired pattern P on the target eye tissue. CPU 92 preferably serves to support control electronics 90, and serves as input for a graphical user interface (GUI) 96 and an alternate user input device 98. GUI 96 allows the user to command various aspects of the system, such as the delivered spot size and pattern, pulse duration and optical power output from treatment light source 12 and aiming light source 16. In addition to the user physically moving slit lamp assembly 3 for gross alignment, the ultimate fine alignment of the light pattern P on the target tissue may be further controlled by use of the input device 98 (which can be a joystick, a touchpad, etc.), which causes mirrors 162, 64 alter their rotations when scanning the light beam thus translating the entire pattern P on the target tissue. This approach yields very fine control of the disposition of the scanned beam. Additional input devices 98 can be included, such as knobs to adjust the output power of the light sources 12, 16, a footswitch or other type of activation device to activate the application of the aiming pattern and/or treatment pattern, etc. The ultimate disposition of the optical output of light sources 12, 16 is intended to be the pattern P contained in the patient's retina R.

The most basic types of patterns P are those formed of discrete, uniformly sized and uniformly spaced fixed spots. The user can use GUI 96 to select, modify, and/or define a number of pattern variables, such as: spot size, spot spacing (i.e. spot density), total number of spots, pattern size and shape, power level, pulse duration, etc. In response, the CPU 92 and control electronics 90 control the treatment light source 12 (assuming it is a pulsed light source) or additionally a shuttering mechanism (not shown) somewhere along the beam 14 to create pulsed treatment light. Mirrors 162, 64 move between pulses to direct each pulse to a discrete location to form a stationary spot.

FIG. 13 is a diagram illustrating how the moving elements of FIG. 8 multiple light sources can be combined into the fiber bundle 32. In this example, an aiming beam and a treatment beam are combined. An aiming beam is used to guide users of the system so they know where to aim the treatment beam on the target.

Although the invention has been described with reference to the above example, it will be understood that modifications and variations are encompassed within the spirit and scope of the invention. Accordingly, the invention is limited only by the following claims.

What is claimed is:

1. An optical device, comprising
a device for generating an optical beam;
a plurality of optical fibers each having an input end, an output end, and a core, wherein each of the optical fibers has a numerical aperture;
a device for moving at least one of the optical fiber input ends and the optical beam relative to each other such that the optical beam selectively enters the input ends one at a time and is transmitted out the output ends one at a time;
wherein the numerical apertures vary among the plurality of optical fibers such that the optical beam transmitted out of the output ends has a varying optical characteristic.

2. The optical device of claim 1, wherein the device for moving at least one of the optical beam and the optical fiber input ends relative to each other comprises a motor configured to translate the optical fiber input ends.

3. The optical device of claim 1, wherein the device for moving at least one of the optical beam and the optical fiber input ends relative to each other comprises a translation stage configured to translate the optical fiber input ends.

4. The optical device of claim 1, wherein the device for moving at least one of the optical beam and the optical fiber input ends relative to each other comprises a movable optical element for deflecting the optical beam relative to the optical fiber input ends.

5. The optical device of claim 4, wherein the movable optical element is a rotatable mirror.

6. The optical device of claim 4, wherein the movable optical element is a translatable curved mirror.

7. The optical device of claim 4, wherein the movable optical element is a translatable lens.

8. The optical device of claim 4, wherein the movable optical element is a movable grating.

9. The optical device of claim 4, wherein the movable optical element is a movable prism.

10. The optical device of claim 1, wherein the device for moving at least one of the optical beam and the optical fiber input ends relative to each other comprises an acousto-optical element for deflecting the optical beam relative to the optical fiber input ends.

11. The optical device of claim 1, wherein the varying optical characteristic is divergence.

12. The optical device of claim 1, wherein the varying optical characteristic is a spot size.

13. The optical device of claim 1, wherein the varying optical characteristic is a spot shape.

14. The optical device of claim 1, wherein the varying optical characteristic is a beam diameter.

15. The device of claim 1, further comprising:
an optical system that is common for the plurality of optical fibers that is configured to receive the optical beam transmitted out of the output ends.

16. The device of claim 15, wherein the common optical system at the output comprises a lens.

17. The device of claim 1, further comprising a lens for focusing the optical beam into the optical fiber input ends.

18. The device of claim 1, further comprising a plurality of optical systems at the output ends, with each of the plurality of optical systems being aligned to only one of the optical fiber output ends.

19. The device of claim 1, further comprising a scanning system to create patterns of light from the optical beam transmitted out of the output ends.

20. The device of claim 1, further comprising an optical magnification element that alters an effective numerical aperture of at least one of the plurality of optical fibers.

21. The device of claim 1, wherein at least two of the optical fibers having a same core diameter and are employed in an aperture-limited arrangement to change an effective NA of the at least one of the optical fibers.

22. The device of claim 1, further comprising an aperture associated with a fiber of the plurality of fibers that is sized to change the effective NA of the fiber, wherein a beam diameter of a beam is adjusted by passing the beam through the fiber and aperture.

23. The device of claim 1, wherein the plurality of optical fibers are maintained in spaced-apart relation from each other.

24. The device of claim 1, wherein the plurality of optical fibers are maintained in a unitary array characterized by sharing an optical system at their output ends.

25. The device of claim 1, wherein the input ends of the plurality of optical fibers are aligned substantially parallel to each other.

26. The device of claim 1, wherein the plurality of optical fibers are arranged in a planar array at their input ends.

27. The device of claim 1, wherein the plurality of optical fibers are arranged parallel to each other in a bundle such that individual fibers abut multiple other individual fibers.

28. The device of claim 27, wherein the output ends of the fibers are grouped into a bundle contained within a ferrule of substantially circular cross-section.

29. The device of claim 1, wherein the optical characteristic of the optical beam transmitted out of one of the output ends is increased or decreased by sending the optical beam through an additional optical fiber.

30. The device of claim 29, wherein the optical characteristic is beam diameter.

31. The device of claim 1, wherein the plurality of optical fibers are bundled at the input ends, but not at the output ends.

32. The device of claim 1, further comprising:
a beam block disposed near the input ends of the optical fibers, wherein the device for moving at least one of the optical fiber input ends and the optical beam is further configured to move at least one of the beam block and the optical beam relative to each other such that the optical beam is selectively incident on the beam block for attenuation purposes.

33. The device of claim 1, wherein each of the output ends of the optical fibers is individually connectorized for compatibility with a different output device.

34. The device of claim 33, wherein the different output device is a slit lamp microscope, a laser indirect ophthamoscope, or a surgical microscope.

35. The device of claim 1, wherein one or more of the optical fibers are split off from the remaining of the optical fibers to attach to the variety of output devices.

36. The device of claim 1, wherein each of the plurality of optical fibers is coupled to its own optical system.

37. A method of varying an optical characteristic of an optical beam, comprising:
   generating an optical beam suitable for transmission by at least one of a plurality of optical fibers that each have an input end, an output end, and a core, wherein each of the optical fibers has a numerical aperture; and
   moving at least one of the optical fiber input ends and the optical beam relative to each other such that the optical beam selectively enters the input ends one at a time and is transmitted out the output ends one at a time;
   wherein the numerical apertures vary among the plurality of optical fibers such that the optical beam transmitted out of the output ends has a varying optical characteristic.

* * * * *